(12) United States Patent
Fleming

(10) Patent No.: US 6,997,050 B2
(45) Date of Patent: Feb. 14, 2006

(54) AERIAL SAMPLER SYSTEM

(75) Inventor: Rex J. Fleming, Boulder, CO (US)

(73) Assignee: University Corporation for Atmospheric Research, Boulder, CO (US)

( * ) Notice: Subject to any disclaimer, the term of this patent is extended or adjusted under 35 U.S.C. 154(b) by 0 days.

(21) Appl. No.: 10/936,969

(22) Filed: Sep. 9, 2004

(65) Prior Publication Data

US 2005/0039516 A1   Feb. 24, 2005

Related U.S. Application Data

(63) Continuation of application No. 10/304,577, filed on Nov. 26, 2002, now Pat. No. 6,809,648.

(51) Int. Cl.
*G01W 1/00* (2006.01)
(52) U.S. Cl. .................. 73/170.01; 340/601
(58) Field of Classification Search ............ 73/170.01, 73/182, 861.07
See application file for complete search history.

(56) References Cited

U.S. PATENT DOCUMENTS

| | | |
|---|---|---|
| 2,970,475 A | 2/1961 | Werner |
| 5,302,026 A | 4/1994 | Phillips |
| 5,544,526 A | 8/1996 | Baltins et al. |
| 5,653,538 A | 8/1997 | Phillips |
| 5,731,507 A | 3/1998 | Hagen et al. |
| 6,070,475 A | 6/2000 | Muehlhauser et al. |
| 6,076,963 A | 6/2000 | Menzies et al. |
| 6,250,149 B1 | 6/2001 | Black |
| 6,269,320 B1 | 7/2001 | Otto |
| 6,609,825 B1 | 8/2003 | Ice et al. |
| 6,672,152 B1 | 1/2004 | Rouse et al. |
| 6,809,648 B1 | 10/2004 | Fleming |

*Primary Examiner*—Edward Lefkowitz
*Assistant Examiner*—Andre Allen
(74) *Attorney, Agent, or Firm*—Setter Ollila LLC

(57) ABSTRACT

A sensor system includes an enclosure mounted externally on an aerial vehicle and a sensor chamber mounted internally within the aerial vehicle. The enclosure receives and converges air particles to cause inertial separation that transfers a first portion of the air particles to a first air transfer path and that causes a second portion of the air particles to bypass the first air transfer path. The first air transfer path transfers the first portion of the air particles from the enclosure to the sensor chamber. The sensor chamber includes at least one sensor that produces sensor data for the first portion of the air particles. A second air transfer path transfers the first portion of the air particles from the sampling chamber to the enclosure. The enclosure transfers the first portion of the air particles and the second portion of the air particles to the atmosphere.

10 Claims, 8 Drawing Sheets

AERIAL SAMPLER SYSTEM

RELATED APPLICATIONS

This patent application is a continuation of patent application Ser. No. 10/304,577; that is entitled "An Aerial Sampler System"; that was filed on Nov. 26, 2002 now U.S. Pat. No. 6,809,648; and that is hereby incorporated by reference into this patent application.

FEDERALLY SPONSORED RESEARCH OR DEVELOPMENT

This invention was made with Government support under Contract number #DTFA01-97-C-00006 awarded by the Federal Aviation Administration. The Government has certain rights in this invention.

MICROFICHE APPENDIX

Not applicable

BACKGROUND OF THE INVENTION

1. Field of the Invention

The invention is related to the fields of aviation and sensors, and in particular, to sensor systems for aerial vehicles.

2. Description of the Prior Art

Aircraft have typically used two fundamental types of air samplers. The first type is called a total air temperature (TAT) probe that obtains total (dynamic) air temperature and static (ambient) air temperature. This TAT probe extends from the aircraft skin about 3 inches, which is away from the friction-heated boundary layer of air next to the aircraft's metal surface. The TAT probe measures the dynamic (total) temperature and obtains the static temperature through the equation:

$$T_T = T_S(1 + 0.2M^2)$$

where $T_T$ is the total temperature;

$T_S$ is the static temperature; and

M is the Mach number which is the fractional speed of the aircraft relative to the speed of sound.

The TAT probe includes a probe heater, which is an FAA requirement due to icing concerns. One problem is the heater tends to fail, which is the highest failure mode of the probes.

The second type of probe is called a pitot tube and is used to measure differential pressure (total minus static) for subsequent calculation of aircraft velocity through Bernoulli's equation:

$$V^2 = 2(P_T - P_S)/\rho$$

where V is velocity;

$P_T$ is total pressure;

$P_S$ is static pressure; and $\rho$ is the density of air, which is a function of atmospheric pressure and temperature.

These two probes work together to provide the information needed for efficient flight. Both types of probes have the common feature of extending away from the airframe to avoid contaminated measurements induced by boundary layer effects near the aircraft's skin. One problem with these two probes is the frictional drag from the extension of both probe from the aircraft's skin. The TAT probe has a frictional drag that is an effective 2.5 lbs. Over time, the cost of additional fuel for such additional weight ranges from $1–$2 per pound per week per aircraft. Another problem arises when the probes are applied to stealth aircrafts. Both of the probes increase the radar cross section, which increases the radar visibility of the aircraft.

Another important measurement for aircraft is water vapor. Water vapor affects virtually all aspects of aviation weather and thus, the safety, efficiency, and capacity of an airspace system. For example, summertime convection is behind most traffic delays. Weather prediction in general, but especially precipitation and severe storm prediction, are crucially dependent upon accurate water vapor profiles in the lower troposphere. The commercial aircraft real-time ascent and descent reports can provide profiles of winds, temperature, and water vapor.

One prior system has used the TAT probe in combination with a water vapor sensing system. FIG. 1 depicts a prior system with the TAT probe and a water vapor sensing system in the prior art. The prior system includes a standard TAT probe to measure total air temperature and static air temperature from the air flow. The water vapor sensing system includes a diode laser to measure the water vapor. This prior system was tested in a prototype mode but never built as a commercial product because of the limited space available within the TAT probe. This forced the use of fiber optic cables to carry the laser light and these induced optical "fringes" that reduced sensitivity of the diode laser measurement technique.

Another prior system uses an "open path" for diode lasers to measure water vapor. The laser transmitter and receiver are external to the aircraft. However, this prior system has accuracy and solar interference problems in addition to the drag concerns.

SUMMARY OF THE INVENTION

Examples of the invention include a sensor system and its method of operation. The sensor system includes an enclosure mounted externally on an aerial vehicle and a sensor chamber mounted internally within the aerial vehicle. The enclosure receives and converges air particles to cause inertial separation that transfers a first portion of the air particles to a first air transfer path and that causes a second portion of the air particles to bypass the first air transfer path. The first air transfer path transfers the first portion of the air particles from the enclosure to the sensor chamber. The sensor chamber includes at least one sensor that produces sensor data for the first portion of the air particles. A second air transfer path transfers the first portion of the air particles from the sampling chamber to the enclosure. The enclosure transfers the first portion of the air particles and the second portion of the air particles to the atmosphere.

BRIEF DESCRIPTION OF THE DRAWINGS

The same reference number represents the same element on all drawings.

FIG. 1 is an illustration of a prior system with a total air temperature probe and a water vapor sensing system in the prior art.

FIG. 2 is an illustration of an aerial sampler system in an example of the invention.

FIG. 3 is a flow chart of an aerial sampler system in an example of the invention.

FIG. 4 is an illustration of a top view of an enclosure in the Fleming Sampler (FS) system in an example of the invention.

FIG. 5 is an illustration of a cross section view of an enclosure in the FS system in an example of the invention.

DETAILED DESCRIPTION OF THE PREFERRED EMBODIMENT

FIGS. 2–8 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 2:
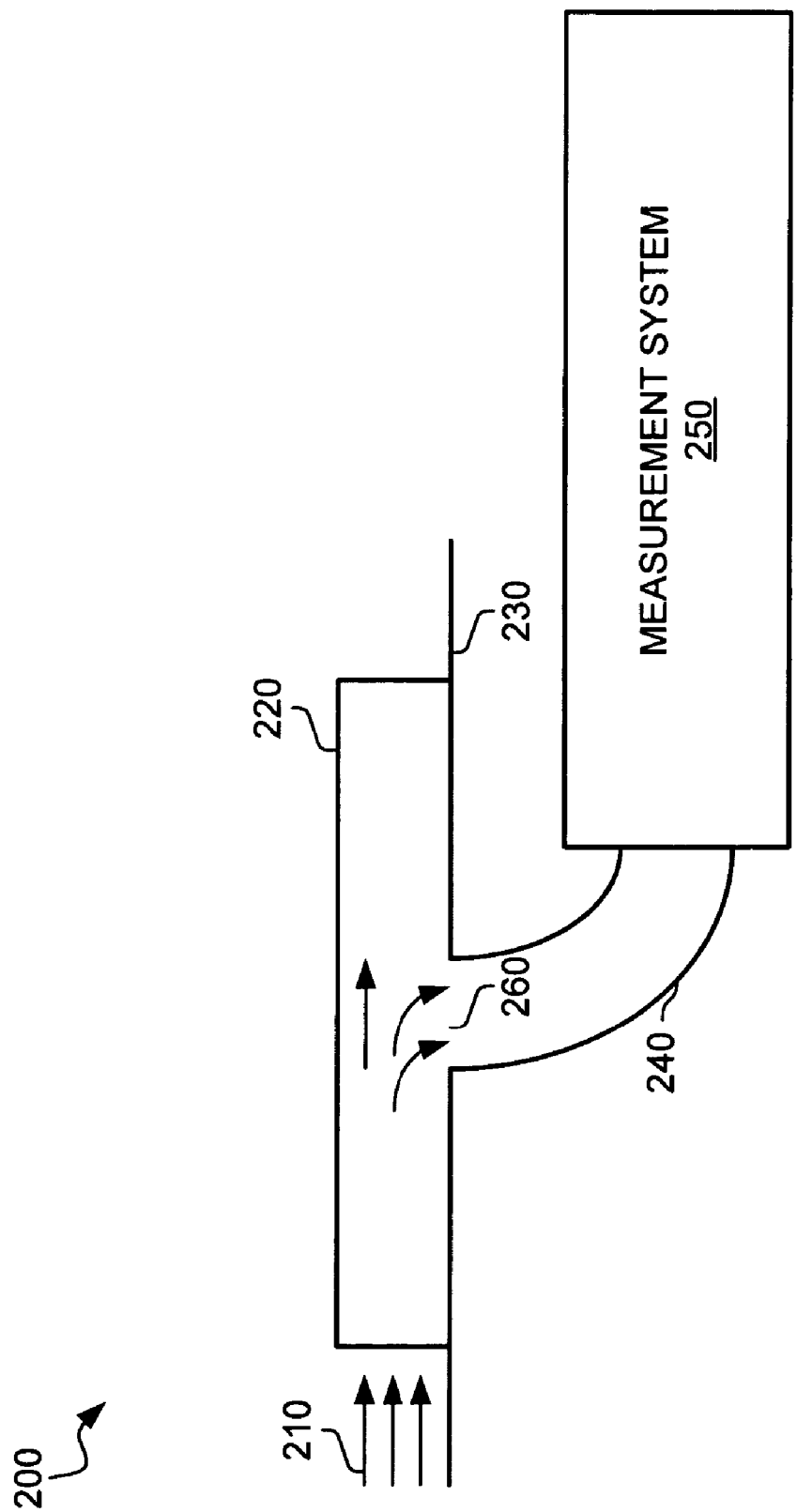
Figure 3:
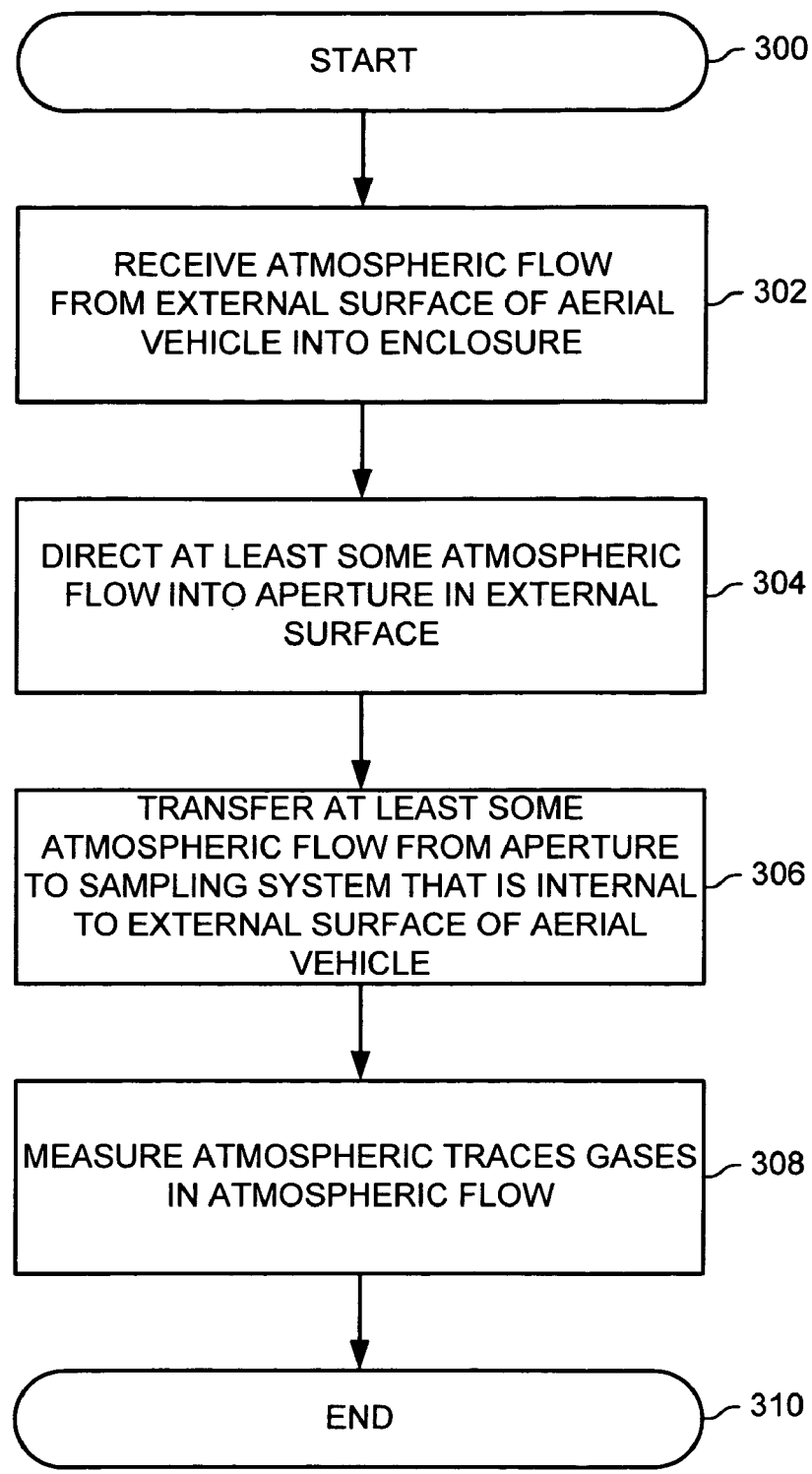

Aerial Sampler System—FIGS. 2–3

FIG. 2 depicts an aerial sampler system 200 in an example of the invention. The aerial sampler system 200 includes an enclosure 220, an external surface 230 of an aerial vehicle, a transfer system 240, and a measurement system 250. The enclosure 220 is located on the external surface 230 of the aerial vehicle. The external surface 230 has an aperture 260. At the aperture 260, the transfer system 240 is connected to the enclosure 220 and the external surface 230 to allow atmospheric flow 210 to enter the transfer system 240. The transfer system 240 is also connected to the measurement system 250.

The atmospheric flow 210 is any flow of trace gases and/or particles that are in a planetary atmosphere. The atmospheric flow 210 typically contains water vapor, which is a trace gas and can vary from 3 to over 40,000 parts per million by volume (ppmv). In one example of the earth's atmosphere, the atmospheric flow contains nitrogen and oxygen gas, water vapor, other trace gases, and particles including aerosols, possible liquid water droplets, and ice crystals. The external surface 230 of an aerial vehicle is the outer layer of an aerial vehicle. In one example, the external surface 230 is the "skin" of a commercial jet aircraft. An aerial vehicle is any object that flies. Some example of aerial vehicles are commercial and military jet aircraft, special purpose manned aircraft, and unmanned aerial vehicles (UAVs).

An enclosure 220 is any configuration of materials that is configured to receive the atmospheric flow 210 from an external surface 230 of an aerial vehicle and direct at least some of the atmospheric flow 210 into an aperture 260 in the external surface 230. One embodiment of the enclosure 220 forms a rib that is shown in FIGS. 4, 5, 6, and 7, which are described below. The transfer system 240 is any device, group of devices, or material that is configured to transfer some of the atmospheric flow 210 from the aperture 260 of an external surface of an aerial vehicle to a measurement system 250. One example of the transfer system 240 is a coupling pipe, which is described below in FIGS. 6, 7, and 8.

Figure 6:
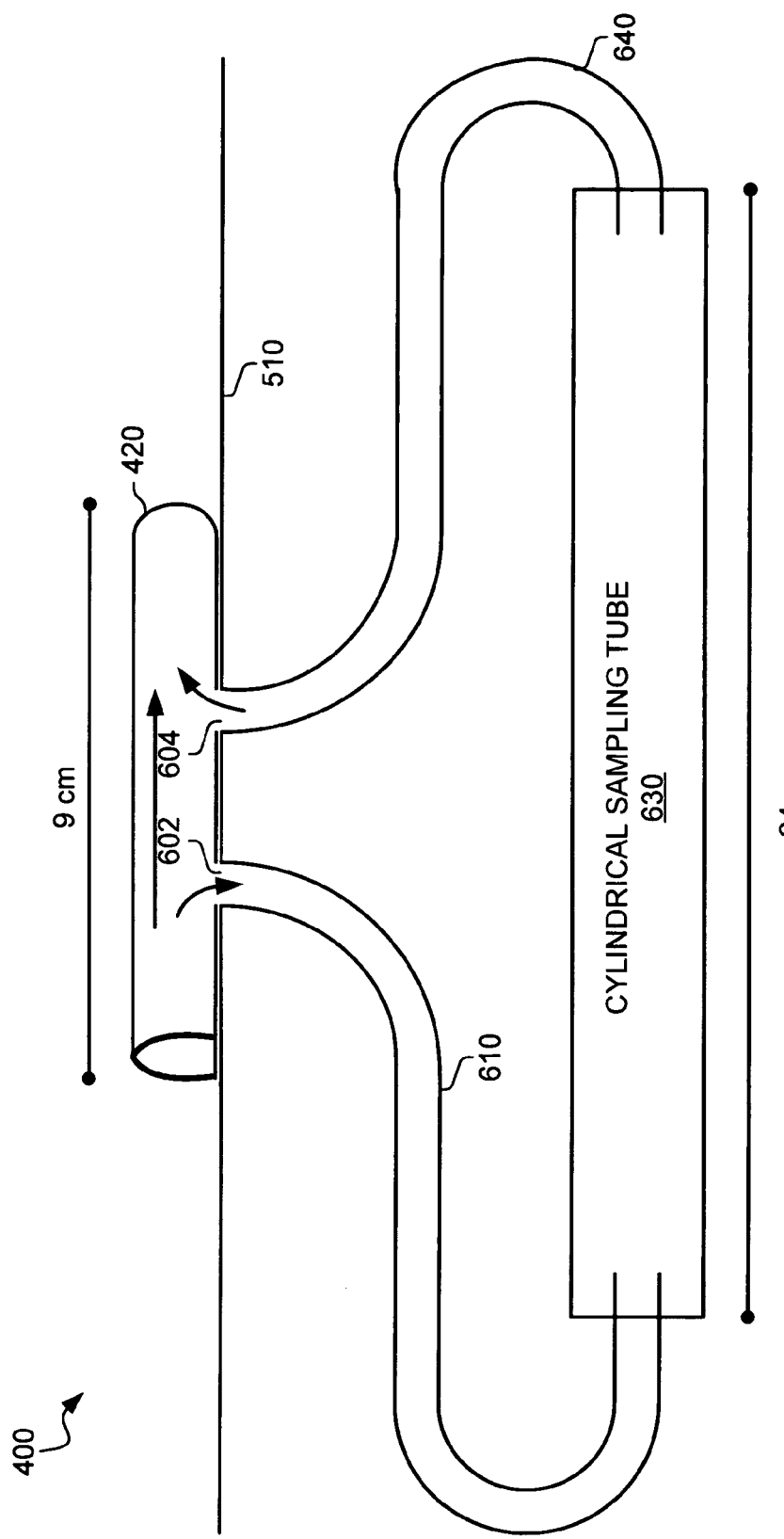
FIG. 6 is an illustration of a side view of the FS system in an example of the invention.
Figure 8:
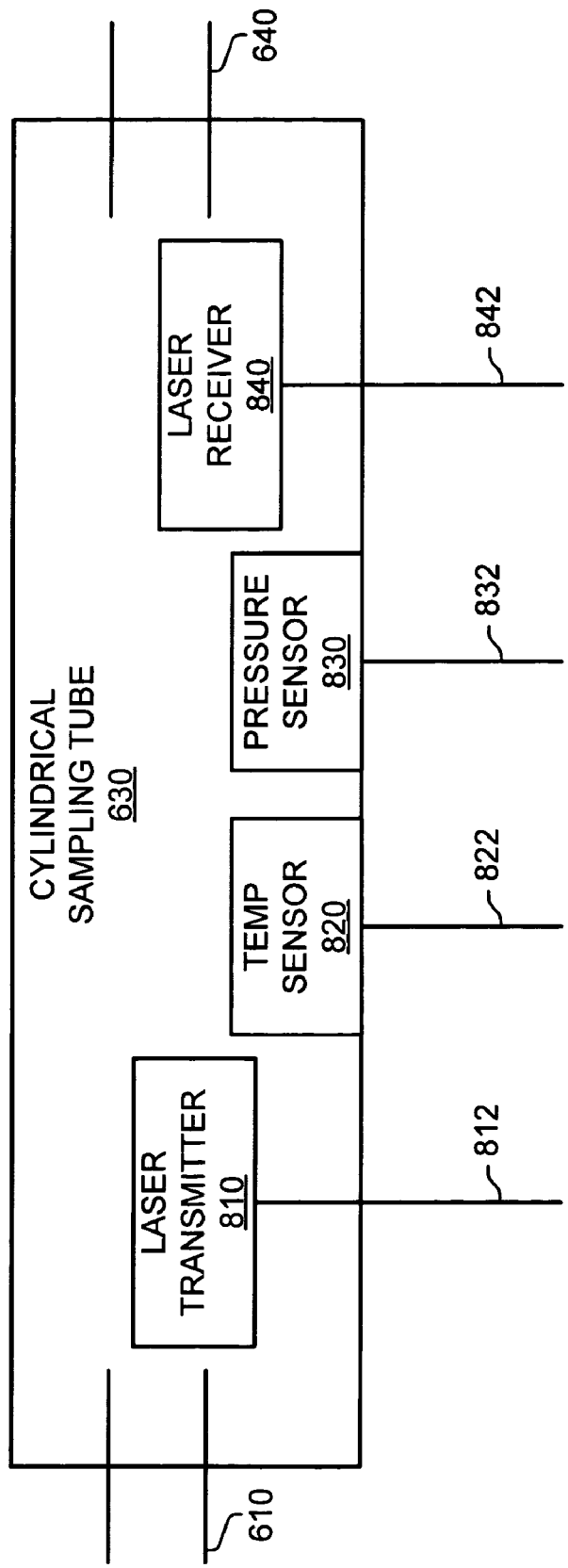
FIG. 8 is an illustration of a cylindrical sampling tube in an example of the invention.

The measurement system 250 is any device, group of devices, or material configured to measure atmospheric trace gases of the atmospheric flow and is internal to an external surface of an aerial vehicle. One example of the measurement system 250 is a cylindrical sampling tube which is shown in FIGS. 6 and 8, which are described below. An example of measuring atmospheric water vapor is described below.

FIG. 3 depicts a flow chart of the aerial sampler system 200 in an example of the invention. FIG. 3 begins in step 300. In step 302, the enclosure 220 receives the atmospheric flow 210 from the external surface 230 of an aerial vehicle. In step 304, the enclosure 220 directs some of the atmospheric flow 210 into the aperture 260 in the external surface 230. In step 306, the transfer system 240 transfers some of the atmospheric flow 210 from the aperture 260 to the measurement system 250 that is internal to the external surface 230 of the aerial vehicle. In step 308, the measurement system 250 measures the atmospheric trace gases of the atmospheric flow 210. FIG. 3 ends in step 310.

The aerial sampler system 200 advantageously measures atmospheric flow from the skin of the aerial vehicle. The aerial sampler system 200 has minimal frictional drag as compared with the TAT probe and the pitot probe. Also, the aerial sampler system 200 does not include any heater as in the TAT probe, which reduces cost, weight, energy consumed, and maintenance for failures. Further advantages for other embodiments are discussed below.

Fleming Sampler System—FIGS. 4–8

Figure 4:
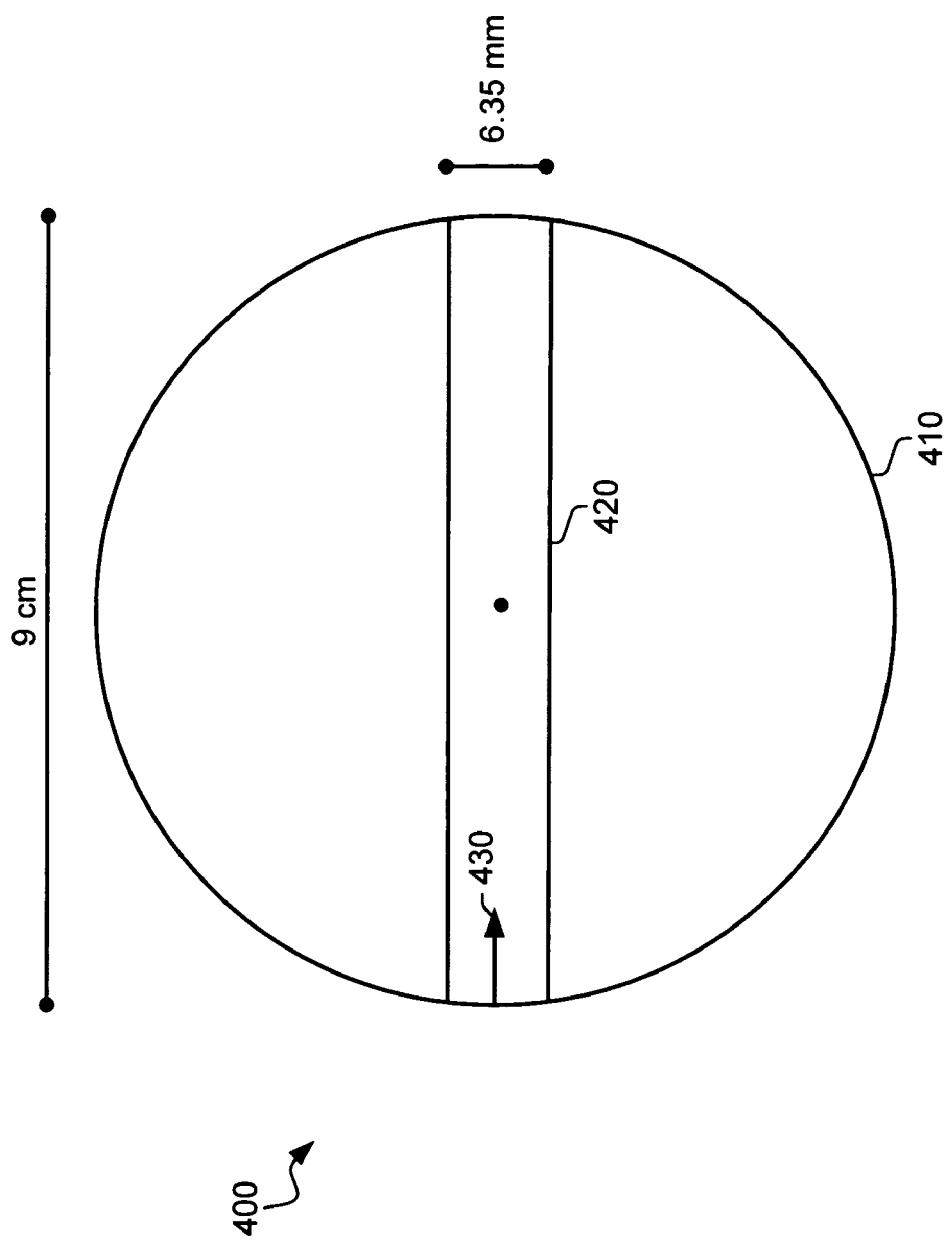

FIG. 4 depicts a top view of an enclosure in a Fleming Sampler (FS) system 400 in an example of the invention. The FS system 400 includes an enclosure 410 that forms a rib 420 on the bottom side of the enclosure. Typically, the rib 420 is not seen from the top view but is shown in FIG. 4 to show the placement of the rib 420 within the enclosure 410. In this embodiment, the enclosure 410 is attached on top of an external plate that has a diameter of approximately 9 cm and the external plate is not shown in FIG. 4. In this embodiment, the enclosure 410 and the external plate are circular. In other embodiments, the enclosure 410 and the external plate could have another shape. The external plate is a metal doubler plate of standard thickness conventionally attached to an airframe. The external plate has two 0.635 cm holes [¼ inch] leading to the interior of the aircraft. The rib 420 has a width of 6.35 mm and a length of approximately 9 cm. The rib 420 extends from left to right across the center of the external plate. In this example, the aircraft is assumed to be moving from right to left. Thus, the air is entering the left side of the rib 420 and exiting the right side or tail of the rib 420. The direction of the air is shown by the arrow 430.

Figure 5:
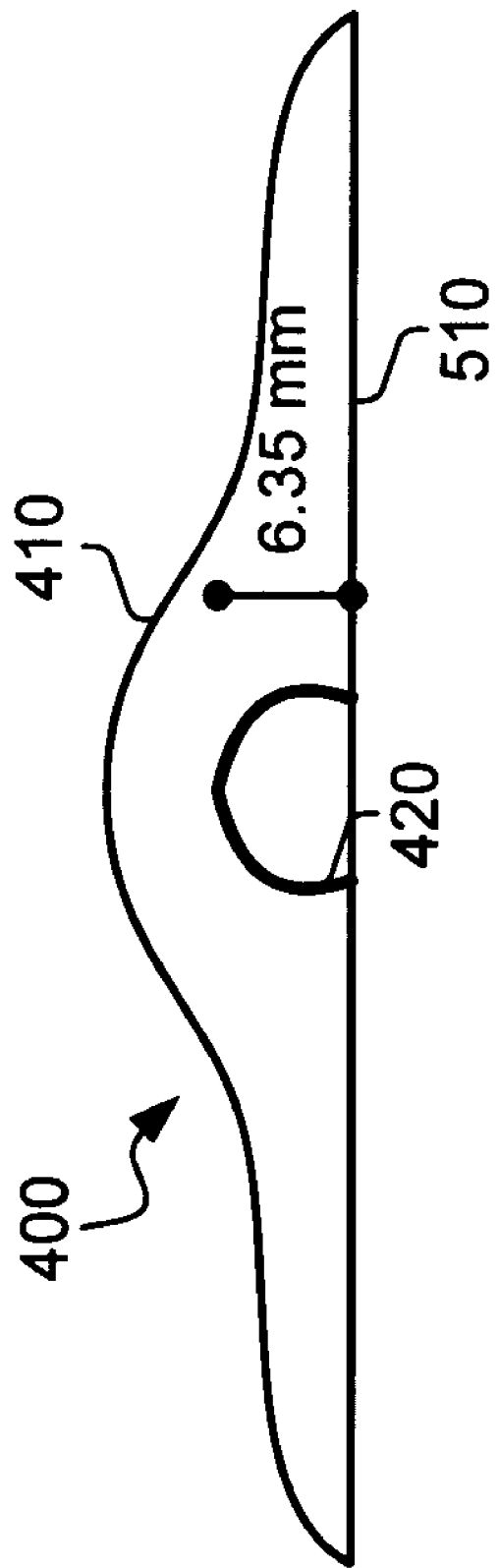

FIG. 5 depicts a cross section view of the enclosure 410 of the FS system 400 in an example of the invention. FIG. 5 depicts the rib 420 located within the enclosure 410, which is attached on top of the external plate 510. In this embodiment, the diameter of the rib 420 is slightly tapered to achieve inertial separation of particles (liquid water droplets, ice crystals, aerosols, etc.) out the tail of the rib 420. The rib 420 has a height of approximately 6.35 mm.

FIG. 6 depicts a side view of FS system 400 in an example of the invention. The FS system 400 includes a rib 420, an external surface 510 of the aircraft, an incoming coupling pipe 610, a cylindrical sampling tube 630, and an outgoing coupling pipe 640. The external plate is not depicted in FIG. 6 for the sake of simplicity and to focus on the flow of atmospheric trace gases to be measured. The rib 420 is attached to the external surface 510 of the aircraft via the external plate. The rib 420, the external plate, and the external surface 510 of the aircraft has an incoming hole 602 and an outgoing hole 604 for air flow. The incoming coupling pipe 610 is connected to the rib 420, the external plate, and the external surface 510 through the incoming hole 602. The opposite end of the incoming coupling pipe 610 is connected to the cylindrical sampling tube 630. The cylindrical sampling tube 630 is also connected to the outgoing coupling tube 640. The outgoing coupling tube 640 is connected to the rib 420, the external plate, and the external surface 510 of the aircraft through the outgoing hole 604.

In this embodiment, the incoming coupling pipe 610 and the outgoing coupling pipe 640 are stainless steel, flexible Kevlar hoses or other hoses of similar material whether fixed or flexible that direct air flow into and out of the cylindrical sampling tube 630. In some embodiments, the incoming coupling pipe 610 and the outgoing coupling pipe 640 may be heated or non-heated. In this embodiment, the cylindrical sampling tube 630 is a stainless steel tube that is 24 cm long. In this embodiment, the cylindrical sampling tube 630 is optimized for an existing diode laser for water vapor measurement, which is described in further detail below in FIG. 8. In another embodiment, the cylindrical sampling tube 630 is 12 cm long with a sapphire-coated mirror at the end that keeps the effective path length 24 cm long. In other embodiments, other reflective material could be in the cylindrical sampling tube 630 to decrease the path length. The diameter of the inlets of the rib 420, the location of the apertures, and the diameter of the cylindrical sampling tube 630 can be altered for other embodiments and optimized for a particular aerial application.

Figure 7:
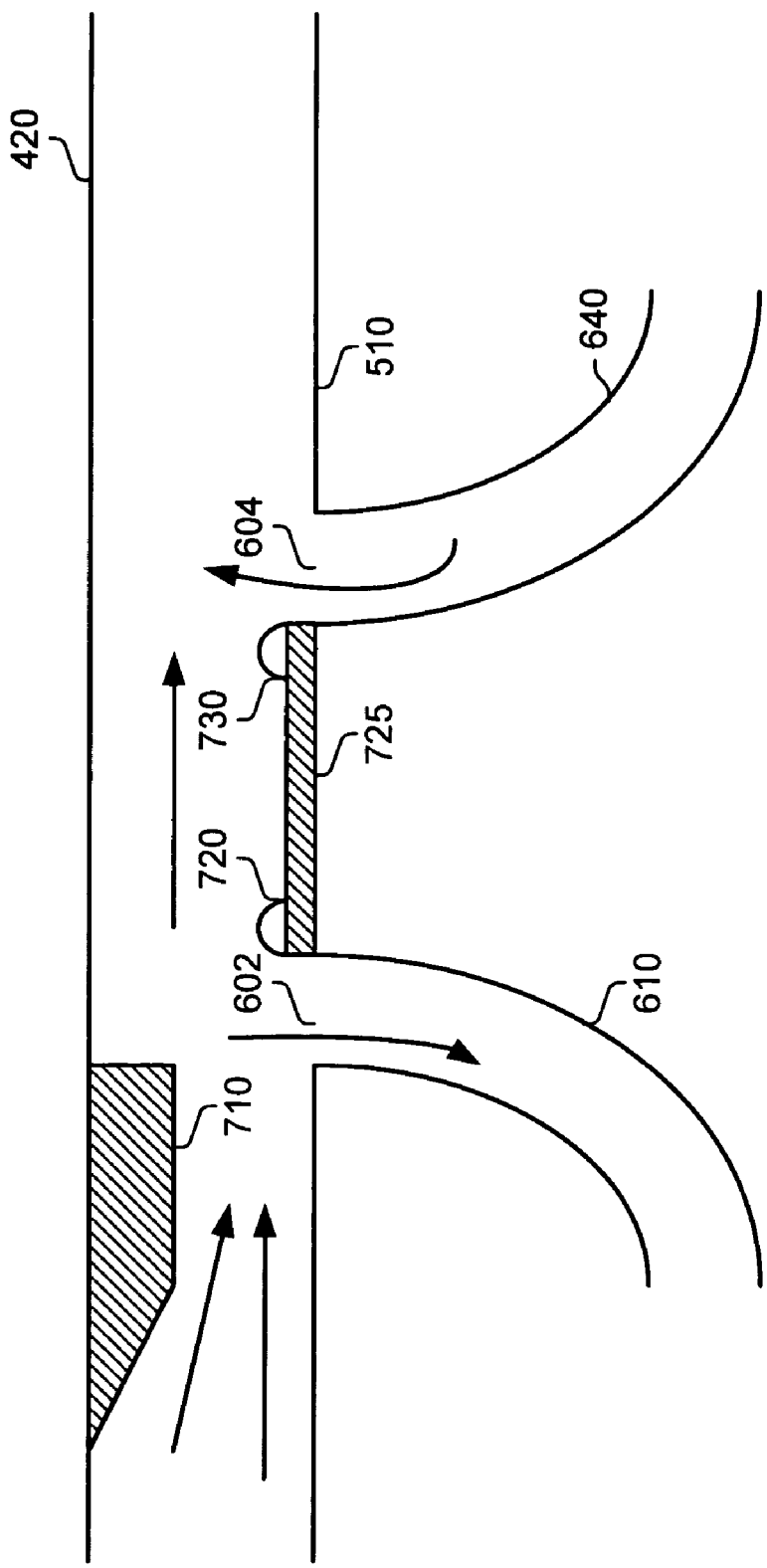
FIG. 7 is an illustration of a detailed side view of the rib of the enclosure, an incoming coupling pipe, and an outgoing coupling pipe in an example of the invention.

FIG. 7 depicts a detailed side view of the rib 420, the incoming coupling pipe 610, and the outgoing coupling pipe 640 in an example of the invention. The rib 420 includes an inertial separator 710. The inertial separator 710 is attached to the top of the rib 420. The inertial separator 710 is a converging metal shape with an approximately 1–2 mm rise. Once again, in this example, the air flows left to right in the rib 420. The inertial separator 710 is configured to converge air flow. The air flow then diverges after the inertial separator 710. The inertial separator 710 forces most particles out the back exit of the rib 420 because of the momentum of the particles (the combination of their density and the fast flow). In other embodiments, there are numerous variations in the height, shape, and position of the inertial separator 710 to converge and then diverge air flow. Also, in other embodiments, the outgoing coupling pipe 640 is attached in various configurations in the aerial vehicle to remove the sampled atmospheric flow from the cylindrical sampling tube 630.

In some embodiments, the rib 420 may include an incoming flow enhancer 720, an outgoing flow enhancer 730, and a base flow enhancer 725. The incoming flow enhancer 720 on top of the base flow enhancer 725 is adjacent to the incoming hole 602. The incoming flow enhancer 720 and the base flow enhancer 725 assist in directing air flow in the incoming hole 602 to the incoming coupling pipe 610. The outgoing flow enhancer 730 on top of the base flow enhancer 725 is adjacent to the outgoing hole 604. The outgoing flow enhancer 730 and the base flow enhancer 725 assist in directing air flow out of the outgoing hole 604 from the outgoing coupling pipe 640. The outgoing flow enhancer 730 and the base flow enhancer 725 prevent the air flow from outgoing hole 604 from going right to left in the opposite direction of the original air flow.

FIG. 8 depicts an illustration of the cylindrical sampling tube 630 in an example of the invention. As discussed above, the cylindrical sampling tube 630 is connected to the incoming coupling pipe 610 and the outgoing coupling pipe 640. The cylindrical tube 630 comprises a laser transmitter 810, a temperature sensor 820, a pressure sensor 830, and a receiver 840.

The cylindrical sampling tube 630 is 24 cm long. This length is sufficiently long for extremely accurate water vapor mixing ratios such as measurements of equivalent relative humidity (RH) as dry as 5% at 40,000 feet. The length is also sufficiently short for the fast-moving air to provide a new sampling volume in a small to large fraction of a second depending upon the aircraft speed. The cylindrical sampling tube 630 also comprises a temperature sensor 820 and a pressure sensor 830 for measuring temperature and pressure, respectively. The temperature sensor 820 and the pressure sensor 830 are mounted on the chamber walls of the cylindrical sampling tube 630. The laser transmitter 810 is a conventional diode laser transmitter configured to transmit laser signals. The receiver 840 is a conventional receiver configured to receive laser signals. In other embodiments, the laser transmitter 810 can be a quantum cascade laser. Measurements of water vapor by diode lasers is disclosed in a publication entitled "Open-Path, Near-Infrared Tunable Diode Laser Spectrometer for Atmospheric Measurement for $H_2O$," by May, R. D., in *the Journal for Geophysical Research*, vol. 103, p. 19,161–19,172 (1998), which is hereby incorporated by reference.

The links 812, 822, 832, and 842 are connected to the laser transmitter 810, the temperature sensor 820, the pressure sensor 830, and the laser receiver 840, respectively. In some embodiments, the links 812, 822, 832, and 842 are connected through a multi-pin connector. In some embodiments, the links 812, 822, 832, and 842 are connected to electronic circuitry, computers, or other processing systems that control, manage and/or process the measurements from the laser transmitter 810, the temperature sensor 820, the pressure sensor 830, and the laser receiver 840. These electronic circuitry, computers, or other processing systems could be located anywhere within the aerial vehicle. Processed information can then be sent to the cockpit and/or to the ground via wireless communications. The measurements could be used in a variety of applications including weather related applications and navigation.

The mixing ratio of atmospheric trace gases may be sampled from the boundary layer of the aircraft because the ultimate intended measurement is unaffected. The laser signal is at a chosen frequency that matches the absorption cross section frequency of the trace gas being measured. Thus, the mixing ratio of water vapor or of some other trace gas can be accurately determined from the lasers, the use of Beer's Law, and measurement of pressure and temperature. It is the measurement of the actual temperature and pressure near the laser light path that makes Beer's law useful. The mixing ratios are conserved properties whether they be determined in static conditions, in fully dynamic or total conditions, or in conditions between the two extremes. Beer's law is:

$$I = I_O \exp(-\sigma n l)$$

where I is light intensity at the detector (receiver);

$I_O$ is the light source intensity; and $(\sigma n l)$ = absorbance where $\sigma$ is the molecular absorption cross section (a function of frequency, pressure, and temperature);

n is the number density of the absorbing species to be measured such as $H_2O$, CO, $CH_4$, $N_2O$, NO, SOx, $O_3$; and l is the path length.

Aerial vehicles may encounter rain, snow, or dense cloud events (water droplets, ice crystals, or a mixture of both) that lead to sensor "wetting." This FS system 400 and the use of a specific laser frequency have a distinct advantage in not being affected by the liquid and solid water elements as such elements do not absorb the laser light at the selected frequency. Only if there were significant amounts of such elements in the cylindrical sampling tube 630 (a situation avoided by the use of the inertial separator 710 in the rib 420 of the FS system 400) would they affect the laser light scattering (not the light absorption) and reduce the sensitivity of the measurement.

In other embodiments, other sampling tubes are added in series to the cylindrical sampling tube 630 so that quantum cascade laser simultaneously measures various chemical or biological species with a different path length that is optimized to match the desired measurement range and consistent with the quantum cascade laser frequency and efficiency.

In one embodiment for an unmanned aerial vehicle such as the large RQ-4A Global Hawk that flies up to 65,000 ft, the FS system 400 measures the water vapor in the stratosphere to a minimum value of 3 ppmv. The usual range in the driest part of the tropical lower stratosphere is typically 3–5 ppmv. In this embodiment, the cylindrical sampling tube 630 is extended to 40 cm.

In another embodiment on the opposite end of the current spectrum of unmanned aerial vehicles such as the small GNAT 750 that has an altitude flight limit of 25,000 feet, the FS system 400 includes the cylindrical sampling tube that is 10 cm. This embodiment accurately measures the full range of expected water vapor mixing ratio values or equivalent RH encountered in the troposphere below 25,000 feet.

In other embodiments, the aircraft could be any unmanned aerial vehicle that operates below 18,000 ft. In this embodiment, the dimensions of the FS system 400 is scaled down by a factor of two except for the length of the cylindrical sampling tube, which is scaled down by a factor of five to ten such as with a path length of 4 to 2 cm. This embodiment achieves a minimum measurement of 1% RH at 18,000 ft. and lower minimum values yet at lower levels of the troposphere.

The FS system 400 has the following advantages. First, the FS system 400 does not include the heater from the TAT probe, which eliminates the costs, weight, energy consumption, and failures associated with the TAT probe. The FS system 400 also has reduced frictional drag as compared with the TAT probe and pitot tube. This may save $1–$2 per pound per week per aircraft, which is a significant cost.

The FS system 400 is also lightweight and efficient as compared to the "open path" prior system. The FS system 400 provides an environment for more accurate measurements of atmospheric trace gases. Also, the FS system 400 does not have the problems of solar interference as in the "open path" prior system. Also, the FS system 400 has less frictional drag than the "open path" prior system.

The FS system 400 also has more sensitivity than the prior system with the TAT probe and the water vapor sensing system by a factor of more than six. This occurs because of the added width and length of the cylindrical sampling tube 630. This eliminates the need for fiber optic laser connections and thus fringes. The measured minimum absorbance improves from $1 \times 10^{-4}$ to $3.75 \times 10^{-5}$—a factor of 2.67 improvement in sensitivity. The added length of the cylindrical sampling tube 630 to 24 cm from 10.2 cm increases the path length by a factor of 2.35. Together, these factors multiply to an improved sensitivity of a factor of 6.2.

The FR system 400 and the use of lasers allows a highly effective water vapor measurement system that can have a significant impact on improving aviation safety, efficiency, and capacity. The FS system 400 and the use of lasers allows water vapor and other trace gas measurements that can contribute to atmospheric science across a spectrum of atmospheric science application ranging from short-term weather predictions to climate change assessments.

The laser light produces accurate water vapor answers even in the presence of aerosols unless the density and number of such aerosols is exceedingly large. If this occurs, the laser intensity (a separate measurement) drops and the software can use information from a second cross cell laser to verify such a condition. These and similar procedures can be shown to lead to further benefits of the FS system 400 in providing an early warning system for volcanic ash (a serious concern for engine performance and hence, safety).

Another application for the FS system 400 is for nuclear-biological-chemical (NBC) terrorism. Mesoscale information from commercial aircraft as part of a composite environmental observing system help mitigate the effects of NBC terrorism. Diode and QC lasers in the FS system 400 provide valuable information for the strategic mesoscale observing system that is now unavailable, and on the tactical observing system that is brought to ground zero should an NBC terrorism event occur. Accurate analysis of atmospheric stability (temperature and water vapor) are required to properly drive plume models. The commercial aircraft can help provide 100 times more stability profiles per day than obtainable from today's balloon-borne radiosonde system. This is the strategic observing system prior to an event. The nature of the tactical observing system is driven by the form of the NBC terrorism event. The identification of the contaminated plume and the environment surrounding it at ground zero can be obtained with special manned aircraft and UAVs with the FS system 400. This would be an important part of the tactical observing system.

In one embodiment for an icing detector, the inlet to the enclosure is made sufficiently small that an icing situation would immediately block the flow into the enclosure. The inertial separator in the enclosure is not needed and is replaced with a pressure sensor. The pressure sensor (which normally would detect full dynamic pressure) would only detect the much weaker static pressure if the hole was blocked by ice build-up. Thus, the detection of ice is performed instantaneously.

The second function of a successful icing detector is to remove the ice extremely rapidly in order to again serve as an icing detector. The time required to remove the ice is what determines the sensor's response time. Of the two known types of icing sensors in use or being developed today, this response time is exceedingly slow (20 or more seconds). The area of ice capture is too large in these sensors and it takes too long to remove the ice through electrical resistance heating. Thus, these sensors have little value in ascent/descent of an aircraft where one would like to know the vertical levels of icing more precisely.

In this embodiment, the enclosure inlet has a thin ring of electrically heated metal surrounding the inlet orifice. This large heat source confined to the miniature ringlet provides a response time of less than 1–2 seconds or a factor of 10 faster than current icing sensors. The sensor information would pass from the enclosure via a multiple pin connector to an external processing system. The processing system includes the heating circuit logic. Heating begins upon ice detection and an immediate cease of heating upon ice removal (pressure back to full dynamic pressure). From the processing system, the information is relayed to the cockpit and to the ground-based personnel in real time like the other application embodiments.

In one embodiment for volcanic ash, the cylindrical sampling tube 630 includes a laser detecting gas from a volcanic eruption and another simple optical laser looking across the cylindrical sampling tube that would confirm that the volcanic aerosol content was sufficiently high. Normally, the inertial separator would remove most aerosol particles—but in a volcanic eruption incident the aircraft may come close enough to the volcanic plume, or to the plume in its subsequently dispersed form, such that the concentration of aerosol particles would be sufficiently dense to override the effects of the inertial separator-leaving a detectable signal. The sensor information would pass from the cylindrical sampling tube 630 via a multiple pin connector and go to an external processing system. From the processing system, the information is relayed to the cockpit and to the ground-based personnel in real-time like the other application embodiments of the invention.

What is claimed is:

1. A device for transfer of a pressure from a pressure prevailing in a first medium onto a second medium, comprising:
    a platform;
    a dividing membrane, which is secured at its edge on said platform, wherein a first surface of said diving membrane, facing away from said platform, can be brought into contact with the first medium, and a second surface of said dividing membrane, facing toward said platform, forms with the platform a pressure chamber, which can be filled with the second medium, said pressure chamber has a pressure chamber opening, through which the pressure can be transmitted by means of the second medium; and
    a sensor for monitoring a material property of the second medium, wherein:
    said sensor is in flow connection with said pressure chamber by way of said pressure chamber opening.

2. The device as claimed in claim 1, wherein:
said sensor is a conductivity sensor.

3. The device as claimed in claim 2, wherein:
said conductivity sensor has a first electrode and a second electrode, which are insulated from one another and from said platform.

4. The device as claimed in claim 2, wherein:
said conductivity sensor has an electrode, which is arranged insulated from said platform, in order to measure the conductivity of the second medium between said electrode and said platform or components conductively connected with said platform.

5. The device as claimed in claim 1, further comprising:
a pressure conducting line, which is in flow connection with said pressure chamber opening.

6. The device as claimed in claim 5, wherein:
said pressure conducting line is a capillary line.

7. The device as claimed in claim 5, further comprising:
a connection adapter, which connects said pressure conducting line with said pressure chamber opening.

8. The device as claimed in claim 5, wherein:
said connection adapter includes said sensor.

9. The device as claimed in claim 1, wherein:
a variable pressure loading of said dividing membrane and/or a volume change of the second medium due to temperature fluctuations within a given working range of the device leads to a flow of the second medium through said pressure chamber opening;
said sensor is arranged at such a distance from said pressure chamber that at least a part of the medium contained in said pressure chamber at 50% of the nominal pressure and at the average temperature of the nominal temperature range of the device flows to the position of said sensor at a compression of said pressure chamber of not more than 30%, preferably not more than 20%, especially preferably not more than 10%.

10. A connection adapter for connecting a pressure line with a pressure transmitter for transfer of a pressure from a pressure prevailing in a first medium onto a second medium, the pressure transmitter having a platform and a dividing membrane, which is secured at its edge on the platform, wherein a first surface of the dividing membrane, facing away from the platform, can be brought into contact with the first medium, and a second surface of the dividing membrane, facing toward the platform, forms with the platform a pressure chamber, which can be filled with the second medium; and wherein the connection adapter comprises:
    a pressure line receiving a pressure transmitter connection for producing a flow connection between the pressure chamber and the pressure line by way of the pressure chamber opening; and
    a sensor for monitoring a material property of the second medium, wherein said sensor is arranged such that it is in flow connection with the pressure chamber through the pressure chamber opening following the connection of the pressure transmitter at said connection adapter.

* * * * *

UNITED STATES PATENT AND TRADEMARK OFFICE
CERTIFICATE OF CORRECTION

PATENT NO. : 6,997,050 B2  
APPLICATION NO. : 10/936969  
DATED : February 14, 2006  
INVENTOR(S) : Rex J. Fleming It is certified that error appears in the above-identified patent and that said Letters Patent is hereby corrected as shown below:

Column 9, lines 24 through 50 and Column 10, lines 1 through 48, cancel all text and replace with the following:

-- 1. A sensor system for an aerial vehicle, the sensor system comprising:
    an enclosure configured to mount externally on the aerial vehicle and receive air particles as the aerial vehicle flies;
    a sensor chamber including at least one sensor and configured to mount internally within the aerial vehicle;
    a first air transfer path coupling the enclosure to the sensor chamber;
    a second air transfer path coupling the sensor chamber to the enclosure;
the enclosure being configured to converge the received air particles to cause inertial separation that transfers a first portion of the air particles to the first air transfer path and that causes a second portion of the air particles to bypass the first air transfer path;
the first air transfer path being configured to transfer the first portion of the air particles from the enclosure to the sensor chamber;
the sensor in the sensor chamber being configured to produce sensor data for the first portion of the air particles;
the second air transfer path being configured to transfer the first portion of the air particles from the sampling chamber to the enclosure; and
the enclosure being configured to receive the first portion of the air particles from the second air transfer path and to transfer the first portion of the air particles and the second portion of the air particles to the atmosphere.

2. The sensor system of claim 1 wherein the enclosure is tapered to converge the received air particles to cause the inertial separation.

3. The sensor system of claim 1 wherein the sensor comprises a temperature sensor configured to detect a temperature of the first portion of the air particles, and wherein the data indicates the temperature.

4. The sensor system of claim 1 wherein the sensor comprises a pressure sensor configured to detect a pressure of the first portion of the air particles, and wherein the data indicates the pressure.

5. The sensor system of claim 1 wherein the first air transfer path comprises a pipe and a plate.

6. The sensor system of claim 1 wherein the second air transfer path comprises a pipe and a plate.

UNITED STATES PATENT AND TRADEMARK OFFICE
CERTIFICATE OF CORRECTION

PATENT NO. : 6,997,050 B2
APPLICATION NO. : 10/936969
DATED : February 14, 2006
INVENTOR(S) : Rex J. Fleming It is certified that error appears in the above-identified patent and that said Letters Patent is hereby corrected as shown below:

7. The sensor system of claim 1 wherein the enclosure is configured with a heated inlet to receive the air particles.

8. The sensor system of claim 1 wherein the enclosure includes a flow enhancer positioned in between the first air transfer path and the second air transfer path.

9. The sensor system of claim 1 wherein the first air transfer path includes a heater.

10. The sensor system of claim 1 wherein the second air transfer path includes a heater.

11. A method of operating a sensor system for an aerial vehicle, the method comprising:
as the aerial vehicle flies, receiving air particles into an enclosure that is externally mounted on the aerial vehicle;
converging the received air particles in the enclosure to cause inertial separation that transfers a first portion of the air particles to a first air transfer path, and that causes a second portion of the air particles to bypass the first air transfer path;
transferring the first portion of the air particles through the first air transfer path from the enclosure to a sensor chamber that is internally mounted within the aerial vehicle;
operating a sensor in the sensor chamber to produce sensor data for the first portion of the air particles;
transferring the first portion of the air particles through a second air transfer path from the sensor chamber to the enclosure; and
transferring the first portion of the air particles and the second portion of the air particles from the enclosure to the atmosphere.

12. The method of claim 11 wherein the enclosure is tapered to converge the received air particles to cause the inertial separation.

13. The method of claim 11 wherein operating the sensor to produce sensor data comprises operating a temperature sensor to detect a temperature of the first portion of the air particles and produce the data to indicate the temperature.

14. The method of claim 11 wherein operating the sensor to produce sensor data comprises operating a pressure sensor to detect a pressure of the first portion of the air particles and produce the data to indicate the pressure.

15. The method of claim 11 wherein the first air transfer path comprises a pipe and a plate.

UNITED STATES PATENT AND TRADEMARK OFFICE
CERTIFICATE OF CORRECTION

PATENT NO. : 6,997,050 B2
APPLICATION NO. : 10/936969
DATED : February 14, 2006
INVENTOR(S) : Rex J. Fleming It is certified that error appears in the above-identified patent and that said Letters Patent is hereby corrected as shown below:

16. The method of claim 11 wherein the second air transfer path comprises a pipe and a plate.

17. The method of claim 11 further comprising heating an inlet on the enclosure that receives the air particles.

18. The method of claim 11 wherein the enclosure includes a flow enhancer positioned in between the first air transfer path and the second air transfer path.

19. The method of claim 11 further comprising heating the first air transfer path.

20. The method of claim 11 further comprising heating the second air transfer path. --

Signed and Sealed this

Nineteenth Day of February, 2008

JON W. DUDAS
*Director of the United States Patent and Trademark Office*

UNITED STATES PATENT AND TRADEMARK OFFICE
CERTIFICATE OF CORRECTION

PATENT NO. : 6,997,050 B2
APPLICATION NO. : 10/936969
DATED : February 14, 2006
INVENTOR(S) : Rex J. Fleming It is certified that error appears in the above-identified patent and that said Letters Patent is hereby corrected as shown below:

Please delete column 1 line 1 through column 10 line 62 and insert column 1 line 1 through column 10 line 62 as attached Signed and Sealed this Twenty Second Day of April, 2008

JON W. DUDAS
*Director of the United States Patent and Trademark Office*

AERIAL SAMPLER SYSTEM

RELATED APPLICATIONS

This patent application is a continuation of patent application Ser. No. 10/304,577; that is entitled "An Aerial Sampler System"; that was filed on Nov. 26, 2002 now U.S. Pat. No. 6,809,648; and that is hereby incorporated by reference into this patent application.

FEDERALLY SPONSORED RESEARCH OR DEVELOPMENT

This invention was made with Government support under Contract number #DTFA01-97-C-00006 awarded by the Federal Aviation Administration. The Government has certain rights in this invention.

MICROFICHE APPENDIX

Not applicable

BACKGROUND OF THE INVENTION

1. Field of the Invention

The invention is related to the fields of aviation and sensors, and in particular, to sensor systems for aerial vehicles.

2. Description of the Prior Art

Aircraft have typically used two fundamental types of air samplers. The first type is called a total air temperature (TAT) probe that obtains total (dynamic) air temperature and static (ambient) air temperature. This TAT probe extends from the aircraft skin about 3 inches, which is away from the friction-heated boundary layer of air next to the aircraft's metal surface. The TAT probe measures the dynamic (total) temperature and obtains the static temperature through the equation:

$$T_T = T_S(1 + 0.2 M^2)$$

where $T_T$ is the total temperature;
$T_S$ is the static temperature; and
M is the Mach number which is the fractional speed of the aircraft relative to the speed of sound.

The TAT probe includes a probe heater, which is an FAA requirement due to icing concerns. One problem is the heater tends to fail, which is the highest failure mode of the probes.

The second type of probe is called a pitot tube and is used to measure differential pressure (total minus static) for subsequent calculation of aircraft velocity through Bernoulli's equation:

$$V^2 = 2(P_T - P_S)/\rho$$

where V is velocity;
$P_T$ is total pressure;
$P_S$ is static pressure; and
$\rho$ is the density of air, which is a function of atmospheric pressure and temperature.

These two probes work together to provide the information needed for efficient flight. Both types of probes have the common feature of extending away from the airframe to avoid contaminated measurements induced by boundary layer effects near the aircraft's skin. One problem with these two probes is the frictional drag from the extension of both probes from the aircraft's skin. The TAT probe has a frictional drag that is an effective 2.5 lbs. Over time, the cost of additional fuel for such additional weight ranges from $1–$2 per pound per week per aircraft. Another problem arises when the probes are applied to stealth aircrafts. Both of the probes increase the radar cross section, which increases the radar visibility of the aircraft.

Another important measurement for aircraft is water vapor. Water vapor affects virtually all aspects of aviation weather and thus, the safety, efficiency, and capacity of an airspace system. For example, summertime convection is behind most traffic delays. Weather prediction in general, but especially precipitation and severe storm prediction, are crucially dependent upon accurate water vapor profiles in the lower troposphere. The commercial aircraft real-time ascent and descent reports can provide profiles of winds, temperature, and water vapor.

Figure 1:
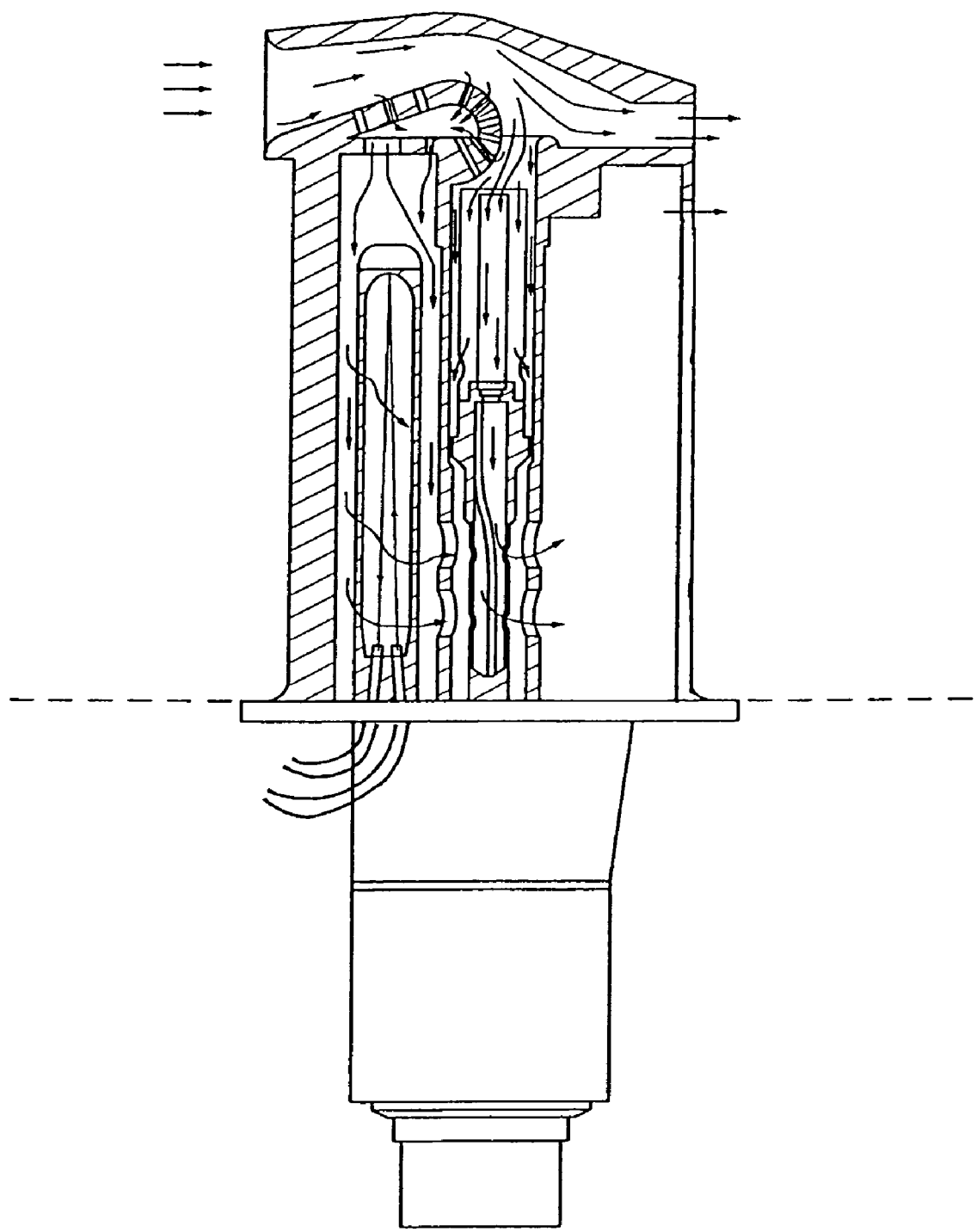

One prior system has used the TAT probe in combination with a water vapor sensing system. FIG. 1 depicts a prior system with the TAT probe and a water vapor sensing system in the prior art. The prior system includes a standard TAT probe to measure total air temperature and static air temperature from the air flow. The water vapor sensing system includes a diode laser to measure the water vapor. This prior system was tested in a prototype mode but never built as a commercial product because of the limited space available within the TAT probe. This forced the use of fiber optic cables to carry the laser light and these induced optical "fringes" that reduced sensitivity of the diode laser measurement technique.

Another prior system uses an "open path" for diode lasers to measure water vapor. The laser transmitter and receiver are external to the aircraft. However, this prior system has accuracy and solar interference problems in addition to the drag concerns.

SUMMARY OF THE INVENTION

Examples of the invention include a sensor system and its method of operation. The sensor system includes an enclosure mounted externally on an aerial vehicle and a sensor chamber mounted internally within the aerial vehicle. The enclosure receives and converges air particles to cause inertial separation that transfers a first portion of the air particles to a first air transfer path and that causes a second portion of the air particles to bypass the first air transfer path. The first air transfer path transfers the first portion of the air particles from the enclosure to the sensor chamber. The sensor chamber includes at least one sensor that produces sensor data for the first portion of the air particles. A second air transfer path transfers the first portion of the air particles from the sampling chamber to the enclosure. The enclosure transfers the first portion of the air particles and the second portion of the air particles to the atmosphere.

BRIEF DESCRIPTION OF THE DRAWINGS

The same reference number represents the same element on all drawings.

FIG. 1 is an illustration of a prior system with a total air temperature probe and a water vapor sensing system in the prior art.

FIG. 2 is an illustration of an aerial sampler system in an example of the invention.

FIG. 3 is a flow chart of an aerial sampler system in an example of the invention.

FIG. 4 is an illustration of a top view of an enclosure in the Fleming Sampler (FS) system in an example of the invention.

FIG. 5 is an illustration of a cross section view of an enclosure in the FS system in an example of the invention.

FIG. 6 is an illustration of a side view of the FS system in an example of the invention.

FIG. 7 is an illustration of a detailed side view of the rib of the enclosure, an incoming coupling pipe, and an outgoing coupling pipe in an example of the invention.

FIG. 8 is an illustration of a cylindrical sampling tube in an example of the invention.

DETAILED DESCRIPTION OF THE PREFERRED EMBODIMENT

FIGS. 2–8 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Aerial Sampler System—FIGS. 2–3

FIG. 2 depicts an aerial sampler system 200 in an example of the invention. The aerial sampler system 200 includes an enclosure 220, an external surface 230 of an aerial vehicle, a transfer system 240, and a measurement system 250. The enclosure 220 is located on the external surface 230 of the aerial vehicle. The external surface 230 has an aperture 260. At the aperture 260, the transfer system 240 is connected to the enclosure 220 and the external surface 230 to allow atmospheric flow 210 to enter the transfer system 240. The transfer system 240 is also connected to the measurement system 250.

The atmospheric flow 210 is any flow of trace gases and/or particles that are in a planetary atmosphere. The atmospheric flow 210 typically contains water vapor, which is a trace gas and can vary from 3 to over 40,000 parts per million by volume (ppmv). In one example of the earth's atmosphere, the atmospheric flow contains nitrogen and oxygen gas, water vapor, other trace gases, and particles including aerosols, possible liquid water droplets, and ice crystals. The external surface 230 of an aerial vehicle is the outer layer of an aerial vehicle. In one example, the external surface 230 is the "skin" of a commercial jet aircraft. An aerial vehicle is any object that flies. Some example of aerial vehicles are commercial and military jet aircraft, special purpose manned aircraft, and unmanned aerial vehicles (UAVs).

An enclosure 220 is any configuration of materials that is configured to receive the atmospheric flow 210 from an external surface 230 of an aerial vehicle and direct at least some of the atmospheric flow 210 into an aperture 260 in the external surface 230. One embodiment of the enclosure 220 forms a rib that is shown in FIGS. 4, 5, 6, and 7, which are described below. The transfer system 240 is any device, group of devices, or material that is configured to transfer some of the atmospheric flow 210 from the aperture 260 of an external surface of an aerial vehicle to a measurement system 250. One example of the transfer system 240 is a coupling pipe, which is described below in FIGS. 6, 7, and 8.

The measurement system 250 is any device, group of devices, or material configured to measure atmospheric trace gases of the atmospheric flow and is internal to an external surface of an aerial vehicle. One example of the measurement system 250 is a cylindrical sampling tube which is shown in FIGS. 6 and 8, which are described below. An example of measuring atmospheric water vapor is described below.

FIG. 3 depicts a flow chart of the aerial sampler system 200 in an example of the invention. FIG. 3 begins in step 300. In step 302, the enclosure 220 receives the atmospheric flow 210 from the external surface 230 of an aerial vehicle. In step 304, the enclosure 220 directs some of the atmospheric flow 210 into the aperture 260 in the external surface 230. In step 306, the transfer system 240 transfers some of the atmospheric flow 210 from the aperture 260 to the measurement system 250 that is internal to the external surface 230 of the aerial vehicle. In step 308, the measurement system 250 measures the atmospheric trace gases of the atmospheric flow 210. FIG. 3 ends in step 310.

The aerial sampler system 200 advantageously measures atmospheric flow from the skin of the aerial vehicle. The aerial sampler system 200 has minimal frictional drag as compared with the TAT probe and the pitot probe. Also, the aerial sampler system 200 does not include any heater as in the TAT probe, which reduces cost, weight, energy consumed, and maintenance for failures. Further advantages for other embodiments are discussed below.

Fleming Sampler System—FIGS. 4–8

FIG. 4 depicts a top view of an enclosure in a Fleming Sampler (FS) system 400 in an example of the invention. The FS system 400 includes an enclosure 410 that forms a rib 420 on the bottom side of the enclosure. Typically, the rib 420 is not seen from the top view but is shown in FIG. 4 to show the placement of the rib 420 within the enclosure 410. In this embodiment, the enclosure 410 is attached on top of an external plate that has a diameter of approximately 9 cm and the external plate is not shown in FIG. 4. In this embodiment, the enclosure 410 and the external plate are circular. In other embodiments, the enclosure 410 and the external plate could have another shape. The external plate is a metal doubler plate of standard thickness conventionally attached to an airframe. The external plate has two 0.635 cm holes [¼ inch] leading to the interior of the aircraft. The rib 420 has a width of 6.35 mm and a length of approximately 9 cm. The rib 420 extends from left to right across the center of the external plate. In this example, the aircraft is assumed to be moving from right to left. Thus, the air is entering the left side of the rib 420 and exiting the right side or tail of the rib 420. The direction of the air is shown by the arrow 430.

FIG. 5 depicts a cross section view of the enclosure 410 of the FS system 400 in an example of the invention. FIG. 5 depicts the rib 420 located within the enclosure 410, which is attached on top of the external plate 510. In this embodiment, the diameter of the rib 420 is slightly tapered to achieve inertial separation of particles (liquid water droplets, ice crystals, aerosols, etc.) out the tail of the rib 420. The rib 420 has a height of approximately 6.35 mm.

FIG. 6 depicts a side view of FS system 400 in an example of the invention. The FS system 400 includes a rib 420, an external surface 510 of the aircraft, an incoming coupling pipe 610, a cylindrical sampling tube 630, and an outgoing coupling pipe 640. The external plate is not depicted in FIG. 6 for the sake of simplicity and to focus on the flow of atmospheric trace gases to be measured. The rib 420 is attached to the external surface 510 of the aircraft via the external plate. The rib 420, the external plate, and the external surface 510 of the aircraft has an incoming hole 602 and an outgoing hole 604 for air flow. The incoming coupling pipe 610 is connected to the rib 420, the external plate, and the external surface 510 through the incoming hole 602. The opposite end of the incoming coupling pipe 610 is connected to the cylindrical sampling tube 630. The cylindrical sampling tube 630 is also connected to the outgoing coupling tube 640. The outgoing coupling tube 640 is connected to the rib 420, the external plate, and the external surface 510 of the aircraft through the outgoing hole 604.

In this embodiment, the incoming coupling pipe 610 and the outgoing coupling pipe 640 are stainless steel, flexible Kevlar hoses or other hoses of similar material whether fixed or flexible that direct air flow into and out of the cylindrical sampling tube 630. In some embodiments, the incoming coupling pipe 610 and the outgoing coupling pipe 640 may be heated or non-heated. In this embodiment, the cylindrical sampling tube 630 is a stainless steel tube that is 24 cm long. In this embodiment, the cylindrical sampling tube 630 is optimized for an existing diode laser for water vapor measurement, which is described in further detail below in FIG. 8. In another embodiment, the cylindrical sampling tube 630 is 12 cm long with a sapphire-coated mirror at the end that keeps the effective path length 24 cm long. In other embodiments, other reflective material could be in the cylindrical sampling tube 630 to decrease the path length. The diameter of the inlets of the rib 420, the location of the apertures, and the diameter of the cylindrical sampling tube 630 can be altered for other embodiments and optimized for a particular aerial application.

FIG. 7 depicts a detailed side view of the rib 420, the incoming coupling pipe 610, and the outgoing coupling pipe 640 in an example of the invention. The rib 420 includes an inertial separator 710. The inertial separator 710 is attached to the top of the rib 420. The inertial separator 710 is a converging metal shape with an approximately 1–2 mm rise. Once again, in this example, the air flows left to right in the rib 420. The inertial separator 710 is configured to converge air flow. The air flow then diverges after the inertial separator 710. The inertial separator 710 forces most particles out the back exit of the rib 420 because of the momentum of the particles (the combination of their density and the fast flow). In other embodiments, there are numerous variations in the height, shape, and position of the inertial separator 710 to converge and then diverge air flow. Also, in other embodiments, the outgoing coupling pipe 640 is attached in various configurations in the aerial vehicle to remove the sampled atmospheric flow from the cylindrical sampling tube 630.

In some embodiments, the rib 420 may include an incoming flow enhancer 720, an outgoing flow enhancer 730, and a base flow enhancer 725. The incoming flow enhancer 720 on top of the base flow enhancer 725 is adjacent to the incoming hole 602. The incoming flow enhancer 720 and the base flow enhancer 725 assist in directing air flow in the incoming hole 602 to the incoming coupling pipe 610. The outgoing flow enhancer 730 on top of the base flow enhancer 725 is adjacent to the outgoing hole 604. The outgoing flow enhancer 730 and the base flow enhancer 725 assist in directing air flow out of the outgoing hole 604 from the outgoing coupling pipe 640. The outgoing flow enhancer 730 and the base flow enhancer 725 prevent the air flow from outgoing hole 604 from going right to left in the opposite direction of the original air flow.

FIG. 8 depicts an illustration of the cylindrical sampling tube 630 in an example of the invention. As discussed above, the cylindrical sampling tube 630 is connected to the incoming coupling pipe 610 and the outgoing coupling pipe 640. The cylindrical tube 630 comprises a laser transmitter 810, a temperature sensor 820, a pressure sensor 830, and a receiver 840.

The cylindrical sampling tube 630 is 24 cm long. This length is sufficiently long for extremely accurate water vapor mixing ratios such as measurements of equivalent relative humidity (RH) as dry as 5% at 40,000 feet. The length is also sufficiently short for the fast-moving air to provide a new sampling volume in a small to large fraction of a second depending upon the aircraft speed. The cylindrical sampling tube 630 also comprises a temperature sensor 820 and a pressure sensor 830 for measuring temperature and pressure, respectively. The temperature sensor 820 and the pressure sensor 830 are mounted on the chamber walls of the cylindrical sampling tube 630. The laser transmitter 810 is a conventional diode laser transmitter configured to transmit laser signals. The receiver 840 is a conventional receiver configured to receive laser signals. In other embodiments, the laser transmitter 810 can be a quantum cascade laser. Measurements of water vapor by diode lasers is disclosed in a publication entitled "Open-Path, Near-Infrared Tunable Diode Laser Spectrometer for Atmospheric Measurement for $H_2O$," by May, R. D., in *the Journal for Geophysical Research*, vol. 103, p. 19,161–19,172 (1998), which is hereby incorporated by reference.

The links 812, 822, 832, and 842 are connected to the laser transmitter 810, the temperature sensor 820, the pressure sensor 830, and the laser receiver 840, respectively. In some embodiments, the links 812, 822, 832, and 842 are connected through a multi-pin connector. In some embodiments, the links 812, 822, 832, and 842 are connected to electronic circuitry, computers, or other processing systems that control, manage and/or process the measurements from the laser transmitter 810, the temperature sensor 820, the pressure sensor 830, and the laser receiver 840. These electronic circuitry, computers, or other processing systems could be located anywhere within the aerial vehicle. Processed information can then be sent to the cockpit and/or to the ground via wireless communications. The measurements could be used in a variety of applications including weather related applications and navigation.

The mixing ratio of atmospheric trace gases may be sampled from the boundary layer of the aircraft because the ultimate intended measurement is unaffected. The laser signal is at a chosen frequency that matches the absorption cross section frequency of the trace gas being measured. Thus, the mixing ratio of water vapor or of some other trace gas can be accurately determined from the lasers, the use of Beer's Law, and measurement of pressure and temperature. It is the measurement of the actual temperature and pressure near the laser light path that makes Beer's law useful. The mixing ratios are conserved properties whether they be determined in static conditions, in fully dynamic or total conditions, or in conditions between the two extremes. Beer's law is:

$$I = I_0 \exp(-\sigma n l)$$

where I is light intensity at the detector (receiver);
$I_0$ is the light source intensity; and
$(\sigma n l)$ = absorbance
where $\sigma$ is the molecular absorption cross section (a function of frequency, pressure, and temperature);
n is the number density of the absorbing species to be measured such as $H_2O$, CO, $CH_4$, $N_2O$, NO, SOx, $O_3$; and
l is the path length.

Aerial vehicles may encounter rain, snow, or dense cloud events (water droplets, ice crystals, or a mixture of both) that lead to sensor "wetting." This FS system 400 and the use of a specific laser frequency have a distinct advantage in not being affected by the liquid and solid water elements as such elements do not absorb the laser light at the selected frequency. Only if there were significant amounts of such elements in the cylindrical sampling tube 630 (a situation avoided by the use of the inertial separator 710 in the rib 420 of the FS system 400) would they affect the laser light scattering (not the light absorption) and reduce the sensitivity of the measurement.

In other embodiments, other sampling tubes are added in series to the cylindrical sampling tube 630 so that quantum cascade laser simultaneously measures various chemical or biological species with a different path length that is optimized to match the desired measurement range and consistent with the quantum cascade laser frequency and efficiency.

In one embodiment for an unmanned aerial vehicle such as the large RQ-4A Global Hawk that flies up to 65,000 ft, the FS system 400 measures the water vapor in the stratosphere to a minimum value of 3 ppmv. The usual range in the driest part of the tropical lower stratosphere is typically 3–5 ppmv. In this embodiment, the cylindrical sampling tube 630 is extended to 40 cm.

In another embodiment on the opposite end of the current spectrum of unmanned aerial vehicles such as the small GNAT 750 that has an altitude flight limit of 25,000 feet, the FS system 400 includes the cylindrical sampling tube that is 10 cm. This embodiment accurately measures the full range of expected water vapor mixing ratio values or equivalent RH encountered in the troposphere below 25,000 feet.

In other embodiments, the aircraft could be any unmanned aerial vehicle that operates below 18,000 ft. In this embodiment, the dimensions of the FS system 400 is scaled down by a factor of two except for the length of the cylindrical sampling tube, which is scaled down by a factor of five to ten such as with a path length of 4 to 2 cm. This embodiment achieves a minimum measurement of 1% RH at 18,000 ft. and lower minimum values yet at lower levels of the troposphere.

The FS system 400 has the following advantages. First, the FS system 400 does not include the heater from the TAT probe, which eliminates the costs, weight, energy consumption, and failures associated with the TAT probe. The FS system 400 also has reduced frictional drag as compared with the TAT probe and pitot tube. This may save $1–$2 per pound per week per aircraft, which is a significant cost.

The FS system 400 is also lightweight and efficient as compared to the "open path" prior system. The FS system 400 provides an environment for more accurate measurements of atmospheric trace gases. Also, the FS system 400 does not have the problems of solar interference as in the "open path" prior system. Also, the FS system 400 has less frictional drag than the "open path" prior system.

The FS system 400 also has more sensitivity than the prior system with the TAT probe and the water vapor sensing system by a factor of more than six. This occurs because of the added width and length of the cylindrical sampling tube 630. This eliminates the need for fiber optic laser connections and thus fringes. The measured minimum absorbance improves from $1 \times 10^{-4}$ to $3.75 \times 10^{-5}$—a factor of 2.67 improvement in sensitivity. The added length of the cylindrical sampling tube 630 to 24 cm from 10.2 cm increases the path length by a factor of 2.35. Together, these factors multiply to an improved sensitivity of a factor of 6.2.

The FR system 400 and the use of lasers allows a highly effective water vapor measurement system that can have a significant impact on improving aviation safety, efficiency, and capacity. The FS system 400 and the use of lasers allows water vapor and other trace gas measurements that can contribute to atmospheric science across a spectrum of atmospheric science application ranging from short-term weather predictions to climate change assessments.

The laser light produces accurate water vapor answers even in the presence of aerosols unless the density and number of such aerosols is exceedingly large. If this occurs, the laser intensity (a separate measurement) drops and the software can use information from a second cross cell laser to verify such a condition. These and similar procedures can be shown to lead to further benefits of the FS system 400 in providing an early warning system for volcanic ash (a serious concern for engine performance and hence, safety).

Another application for the FS system 400 is for nuclear-biological-chemical (NBC) terrorism. Mesoscale information from commercial aircraft as part of a composite environmental observing system help mitigate the effects of NBC terrorism. Diode and QC lasers in the FS system 400 provide valuable information for the strategic mesoscale observing system that is now unavailable, and on the tactical observing system that is brought to ground zero should an NBC terrorism event occur. Accurate analysis of atmospheric stability (temperature and water vapor) are required to properly drive plume models. The commercial aircraft can help provide 100 times more stability profiles per day than obtainable from today's balloon-borne radiosonde system. This is the strategic observing system prior to an event. The nature of the tactical observing system is driven by the form of the NBC terrorism event. The identification of the contaminated plume and the environment surrounding it at ground zero can be obtained with special manned aircraft and UAVs with the FS system 400. This would be an important part of the tactical observing system.

In one embodiment for an icing detector, the inlet to the enclosure is made sufficiently small that an icing situation would immediately block the flow into the enclosure. The inertial separator in the enclosure is not needed and is replaced with a pressure sensor. The pressure sensor (which normally would detect full dynamic pressure) would only detect the much weaker static pressure if the hole was blocked by ice build-up. Thus, the detection of ice is performed instantaneously.

The second function of a successful icing detector is to remove the ice extremely rapidly in order to again serve as an icing detector. The time required to remove the ice is what determines the sensor's response time. Of the two known types of icing sensors in use or being developed today, this response time is exceedingly slow (20 or more seconds). The area of ice capture is too large in these sensors and it takes too long to remove the ice through electrical resistance heating. Thus, these sensors have little value in ascent/descent of an aircraft where one would like to know the vertical levels of icing more precisely.

In this embodiment, the enclosure inlet has a thin ring of electrically heated metal surrounding the inlet orifice. This large heat source confined to the miniature ringlet provides a response time of less than 1–2 seconds or a factor of 10 faster than current icing sensors. The sensor information would pass from the enclosure via a multiple pin connector to an external processing system. The processing system includes the heating circuit logic. Heating begins upon ice detection and an immediate cease of heating upon ice removal (pressure back to full dynamic pressure). From the processing system, the information is relayed to the cockpit and to the ground-based personnel in real time like the other application embodiments.

In one embodiment for volcanic ash, the cylindrical sampling tube 630 includes a laser detecting gas from a volcanic eruption and another simple optical laser looking across the cylindrical sampling tube that would confirm that the volcanic aerosol content was sufficiently high. Normally, the inertial separator would remove most aerosol particles—but in a volcanic eruption incident the aircraft may come close enough to the volcanic plume, or to the plume in its subsequently dispersed form, such that the concentration of aerosol particles would be sufficiently dense to override the effects of the inertial separator-leaving a detectable signal. The sensor information would pass from the cylindrical sampling tube 630 via a multiple pin connector and go to an external processing system. From the processing system, the information is relayed to the cockpit and to the ground-based personnel in real-time like the other application embodiments of the invention.

What is claimed is:

1. A sensor system for an aerial vehicle, the sensor system comprising:
   an enclosure configured to mount externally on the aerial vehicle and receive air particles as the aerial vehicle flies;
   a sensor chamber including at least one sensor and configured to mount internally within the aerial vehicle;
   a first air transfer path coupling the enclosure to the sensor chamber;
   a second air transfer path coupling the sensor chamber to the enclosure;
   the enclosure being configured to converge the received air particles to cause inertial separation that transfers a first portion of the air particles to the first air transfer path and that causes a second portion of the air particles to bypass the first air transfer path;
   the first air transfer path being configured to transfer the first portion of the air particles from the enclosure to the sensor chamber;
   the sensor in the sensor chamber being configured to produce sensor data for the first portion of the air particles;
   the second air transfer path being configured to transfer the first portion of the air particles from the sampling chamber to the enclosure; and
   the enclosure being configured to receive the first portion of the air particles from the second air transfer path and to transfer the first portion of the air particles and the second portion of the air particles to the atmosphere.

2. The sensor system of claim 1 wherein the enclosure is tapered to converge the received air particles to cause the inertial separation.

3. The sensor system of claim 1 wherein the sensor comprises a temperature sensor configured to detect a temperature of the first portion of the air particles, and wherein the data indicates the temperature.

4. The sensor system of claim 1 wherein the sensor comprises a pressure sensor configured to detect a pressure of the first portion of the air particles, and wherein the data indicates the pressure.

5. The sensor system of claim 1 wherein the first air transfer path comprises a pipe and a plate.

6. The sensor system of claim 1 wherein the second air transfer path comprises a pipe and a plate.

7. The sensor system of claim 1 wherein the enclosure is configured with a heated inlet to receive the air particles.

8. The sensor system of claim 1 wherein the enclosure includes a flow enhancer positioned in between the first air transfer path and the second air transfer path.

9. The sensor system of claim 1 wherein the first air transfer path includes a heater.

10. The sensor system of claim 1 wherein the second air transfer path includes a heater.

11. A method of operating a sensor system for an aerial vehicle, the method comprising:
   as the aerial vehicle flies, receiving air particles into an enclosure that is externally mounted on the aerial vehicle;
   converging the received air particles in the enclosure to cause inertial separation that transfers a first portion of the air particles to a first air transfer path, and that causes a second portion of the air particles to bypass the first air transfer path;
   transferring the first portion of the air particles through the first air transfer path from the enclosure to a sensor chamber that is internally mounted within the aerial vehicle;
   operating a sensor in the sensor chamber to produce sensor data for the first portion of the air particles;
   transferring the first portion of the air particles through a second air transfer path from the sensor chamber to the enclosure; and
   transferring the first portion of the air particles and the second portion of the air particles from the enclosure to the atmosphere.

12. The method of claim 11 wherein the enclosure is tapered to converge the received air particles to cause the inertial separation.

13. The method of claim 11 wherein operating the sensor to produce sensor data comprises operating a temperature sensor to detect a temperature of the first portion of the air particles and produce the data to indicate the temperature.

14. The method of claim 11 wherein operating the sensor to produce sensor data comprises operating a pressure sensor to detect a pressure of the first portion of the air particles and produce the data to indicate the pressure.

15. The method of claim 11 wherein the first air transfer path comprises a pipe and a plate.

16. The method of claim 11 wherein the second air transfer path comprises a pipe and a plate.

17. The method of claim 11 further comprising heating an inlet on the enclosure that receives the air particles.

18. The method of claim 11 wherein the enclosure includes a flow enhancer positioned in between the first air transfer path and the second air transfer path.

19. The method of claim 11 further comprising heating the first air transfer path.

20. The method of claim 11 further comprising heating the second air transfer path.

* * * * *